US010146232B2

United States Patent
Buell (10) Patent No.: US 10,146,232 B2
(45) Date of Patent: Dec. 4, 2018

(54) MODULAR ADAPTOR FOR MONITORING DISPENSER ACTIVITY

(71) Applicant: GOJO Industries, Inc., Akron, OH (US)

(72) Inventor: Shelby Jay Buell, Medina, OH (US)

(73) Assignee: GOJO Industries, Inc., Akron, OH (US)

( * ) Notice: Subject to any disclaimer, the term of this patent is extended or adjusted under 35 U.S.C. 154(b) by 130 days.

(21) Appl. No.: 15/035,321

(22) PCT Filed: Nov. 7, 2014

(86) PCT No.: PCT/US2014/064544
§ 371 (c)(1),
(2) Date: May 9, 2016

(87) PCT Pub. No.: WO2015/070016
PCT Pub. Date: May 14, 2015

(65) Prior Publication Data
US 2016/0274596 A1    Sep. 22, 2016

Related U.S. Application Data

(60) Provisional application No. 61/901,885, filed on Nov. 8, 2013.

(51) Int. Cl.
*A47K 5/12*    (2006.01)
*G05D 7/06*    (2006.01)
*G05B 15/02*    (2006.01)
*G16H 40/20*    (2018.01)

(52) U.S. Cl.
CPC ............. *G05D 7/0676* (2013.01); *A47K 5/12* (2013.01); *A47K 5/1217* (2013.01); *G05B 15/02* (2013.01); *G16H 40/20* (2018.01)

(58) Field of Classification Search
CPC ..... A47K 5/1217; B05B 11/308; G16H 40/20
See application file for complete search history.

(56) References Cited

U.S. PATENT DOCUMENTS

| 5,421,489 A | 6/1995 | Holzner et al. |
| 2005/0139617 A1* | 6/2005 | Lewis ................. A47K 5/1204 222/333 |
| 2007/0257803 A1* | 11/2007 | Munro ................ G08B 21/245 340/573.1 |
| 2008/0019489 A1 | 1/2008 | Lynn |

(Continued)

OTHER PUBLICATIONS

International Search Report cited in PCT Application No. PCT/US14/64544 dated May 11, 2015, pp. 1-11.

(Continued)

*Primary Examiner* — Thomas L Dickey
(74) *Attorney, Agent, or Firm* — Cooper Legal Group, LLC (57) ABSTRACT

A data collection module for capturing dispense event information from an associated fluid dispenser is provided. In some embodiments, the data collection module includes a detection instrument for detecting activation of a dispenser actuator of the fluid dispenser and for generating an output indicating activation of the dispenser actuator. In some embodiments, the data collection module includes digital electronic circuitry for communicating the data to an associated external network.

20 Claims, 11 Drawing Sheets

(56) References Cited

U.S. PATENT DOCUMENTS

2013/0076514 A1  3/2013  Wegelin et al.
2013/0257615 A1* 10/2013 Iseri ...................... G08B 21/18
                                                            340/540

OTHER PUBLICATIONS

EP Communication cited in EP Application No. 14815955.1 dated Nov. 24, 2011, 4 pgs.
EP Communication cited in U.S. Appl. No. 14 815 955.1 dated Apr. 3, 2018, 5 pgs.

* cited by examiner

MODULAR ADAPTOR FOR MONITORING DISPENSER ACTIVITY

RELATED APPLICATIONS

This application claims priority to U.S. Provisional Application 61/901,885, titled "MODULAR ADAPTOR FOR MONITORING DISPENSER ACTIVITY" and filed on Nov. 8, 2013, which is incorporated herein by reference.

FIELD OF THE INVENTION

The current invention pertains to devices for monitoring fluid product dispenser usage, and more specifically to fluid dispensers that can be retrofitted with data collection modules.

BACKGROUND OF THE INVENTION

People entering healthcare facilities, like for example hospitals or nursing homes, frequently acquire infections during the course of their stay. Such infections, which the patients did not originally possess prior to entering the healthcare facility, are termed HAIs (Healthcare-Associated Infections) and represent a serious risk to the health of the patient. In many instances, HAIs result in prolonged stay and additional treatment, and in other instances even loss of life. In addition to the trauma imposed on the patient and their family, HAIs add significant financial burden to the healthcare facility, which incurs the cost of treatment.

There is significant evidence that good hand hygiene can prevent the spread of HAIs. Washing with soap and clean water assist in preventing the transmission of germs, as does the use hand sanitizers. Results from studies have lead health organizations like the CDC (Center For Disease Control) and the WHO (World Health Organization) to release guidelines for cleaning and sanitizing hands, which include the use of alcohol based sanitizers. Placement and usage of hand sanitizing stations have thus become common throughout the healthcare industry.

Despite the advertised benefits and access to sanitizer, health care workers (HCWs) still do not consistently follow published guidelines for good hand hygiene. Numerous methods and devices have therefore been developed to monitor the hand hygiene activities of HCWs and other personnel for encouraging proper hand hygiene. Some systems, like Activity Monitoring Systems, incorporate data collection modules into hand sanitizing dispensers, which logs dispensing activity. Other monitoring systems log dispensing data and correlate the data to healthcare workers. These systems are referred to as Real Time Location Systems (RTLS).

However, monitoring systems can be costly to implement and some healthcare facilities, while convinced of the benefits of hand sanitization, are not ready to invest in the hardware needed to track compliance to hand hygiene guidelines. It would therefore be advantageous to provide hand sanitizing dispensers that could be easily retrofitted with the hardware necessary for tracking dispensers usage when the user is ready.

SUMMARY OF THE INVENTION

According to one embodiment of the subject invention a fluid dispensing system includes a dispenser housing having walls that support a fluid reservoir and a pump. The dispenser housing includes a mounting bracket extending from a posterior side and a dispenser actuator attached to the anterior side of the dispenser housing. The dispenser actuator is moveably connected to the dispenser housing and engages a pump for use in dispensing fluid product. A mounting plate is provided having first and second sides. The first side of the mounting plate includes a first mounting surface for attaching the mounting plate to a structure, which may be a wall or counter. The second side of the mounting plate includes a second mounting surface adapted to receive the mounting bracket for supporting the dispenser housing. A data collection module is configured to selectively mount between the dispenser housing and the mounting plate. The data collection module may include a detection instrument detecting activation of the dispenser actuator when the data collection module is attached to the dispenser housing. The detection instrument has an output indicating activation of the dispenser actuator. Digital electronic circuitry is also provided and includes memory for storing data representing the output indicating activation of the dispenser actuator. Lastly, a processor, which may be a microprocessor, may be incorporated for use in communicating said data to an associated external device.

According to another embodiment of the subject invention, a data collection module is described which captures dispense event information from a fluid dispenser. The fluid dispenser includes a dispenser housing and a dispenser actuator. The data collection module includes a housing having one or more walls defining an enclosure. The module housing includes a first mounting support for connecting the module housing to the fluid dispenser and a second mounting support for connecting the module housing to a structure. The data collection module further includes a detection instrument for detecting activation of the dispenser actuator when the data collection module is attached to the dispenser housing. The detection instrument has an output indicating activation of the dispenser actuator. Digital electronic circuitry includes memory for storing data representing the output (where the output indicates activation of the dispenser actuator) and a processor for communicating the data to an external network. The digital electronic circuitry is received at least partially within the enclosure and may be accompanied by an electrical power storage device connected to supply electrical power to the digital electronic circuitry.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings.

DETAILED DESCRIPTION

Figure 1:
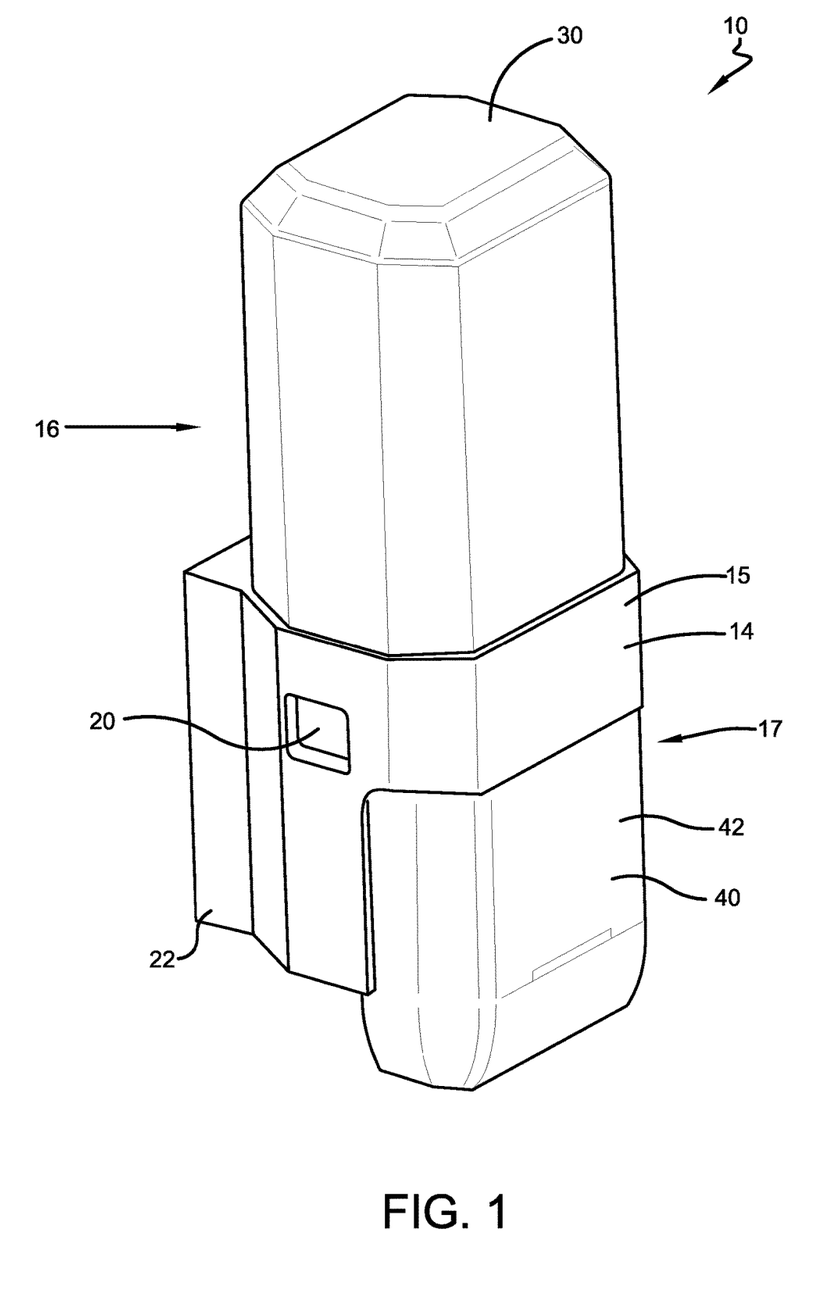
FIG. 1 depicts a front-side perspective view of a fluid dispenser attached to a wall structure according to the embodiments of the subject invention.

A product dispenser is depicted in FIG. 1 that doles out a measured amount of product according to the embodiments of the subject invention. In one exemplary instance, the product dispenser, shown generally at 10, dispenses hand care products like soap, lotion or sanitizers, although other products may similarly be dispensed from the product dispenser.

The product dispenser 10 includes a dispenser housing 14 made of one or more dispenser walls 15 constructed to support the components of the dispenser. Plastic may be used for cost effective manufacturing of the dispenser housing 14, as well as other components of the dispenser 10. At a rear side 16 of the dispenser 10, a mounting bracket 22 is included for attaching the dispenser to wall (not shown), dispenser stand 19 or other supporting structure. The mounting bracket 22, as shown, is integrally fashioned with the dispenser housing 14. However, other configurations are contemplated that have a mounting bracket 22 that fastens to the dispenser housing.

Figure 2:
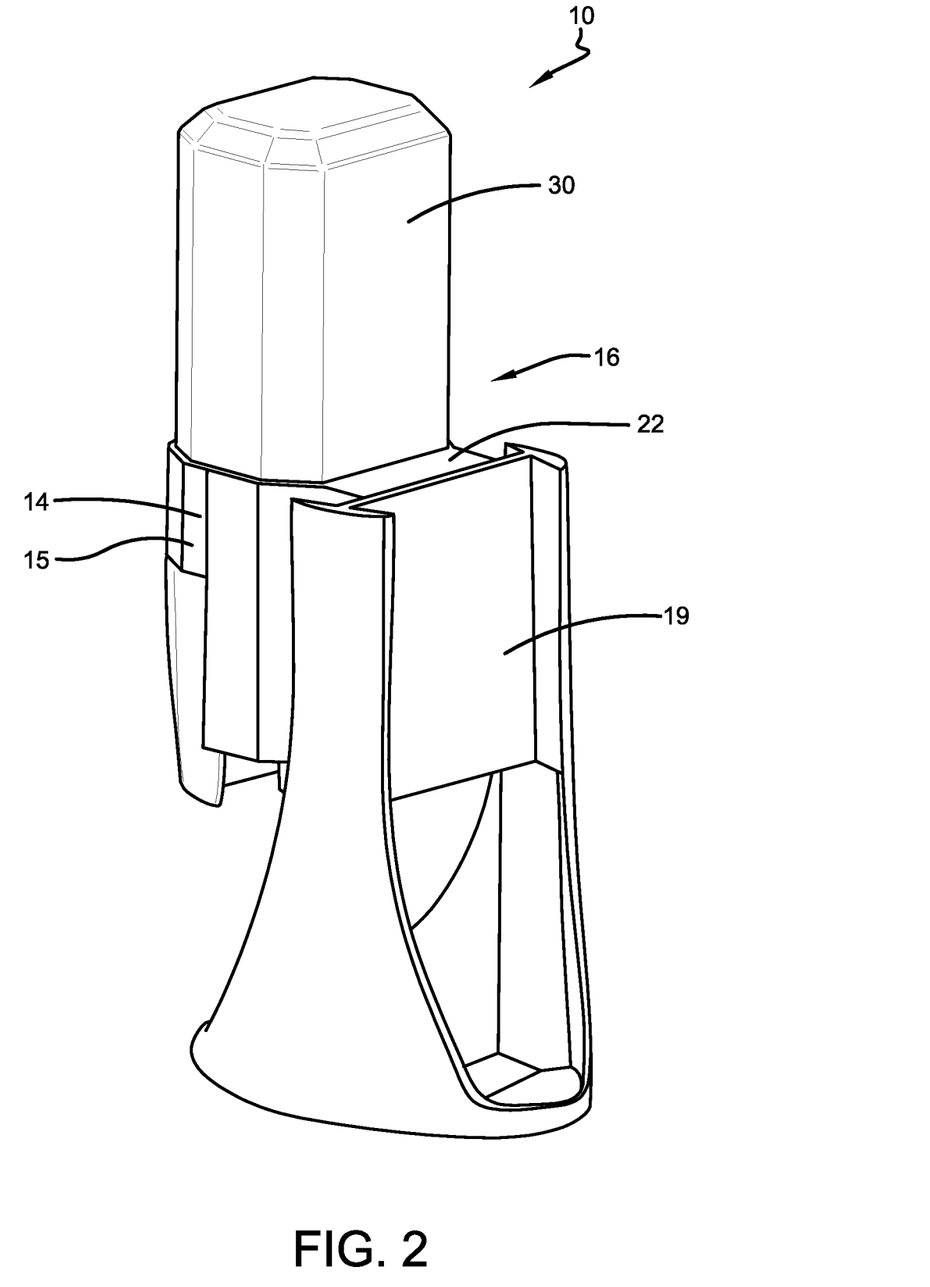
FIG. 2 depicts a rear-side perspective view of a fluid dispenser attached to a stand according to the embodiments of the subject invention.
Figure 2A:
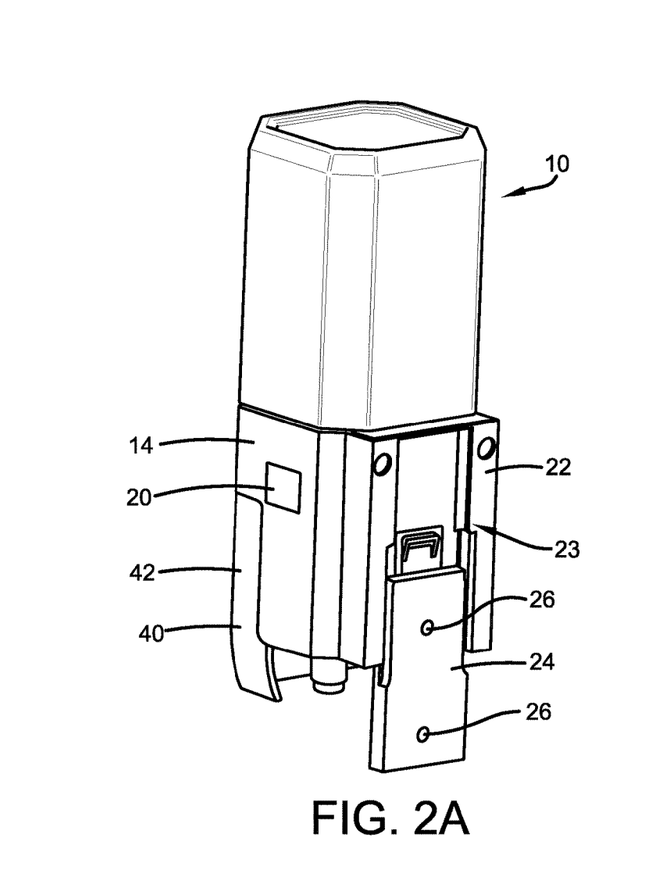
FIG. 2a depicts a rear-side perspective view of a fluid dispenser and mounting plate according to the embodiments of the subject invention.
Figure 2B:
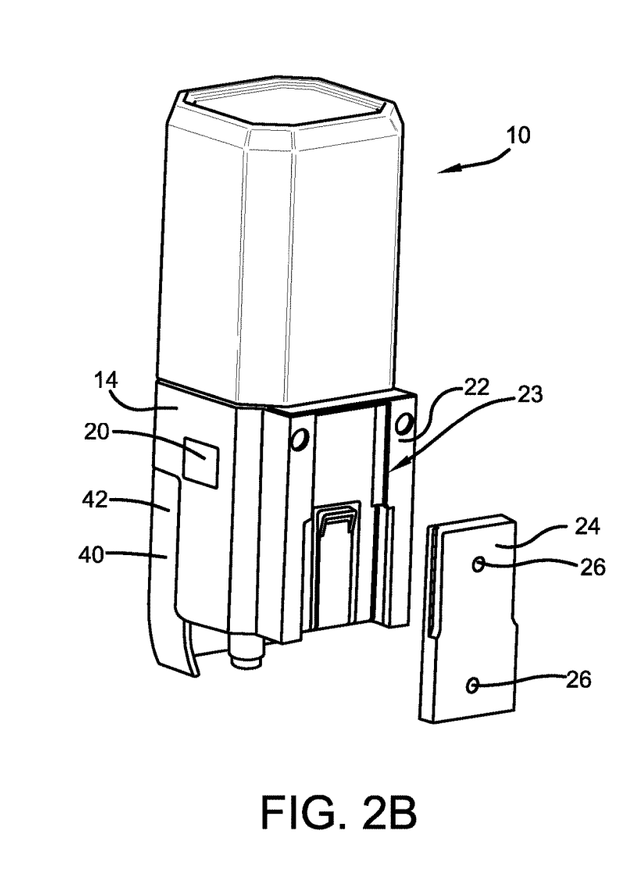
FIG. 2b depicts another rear-side perspective view of a fluid dispenser and mounting plate according to the embodiments of the subject invention.
Figure 2C:
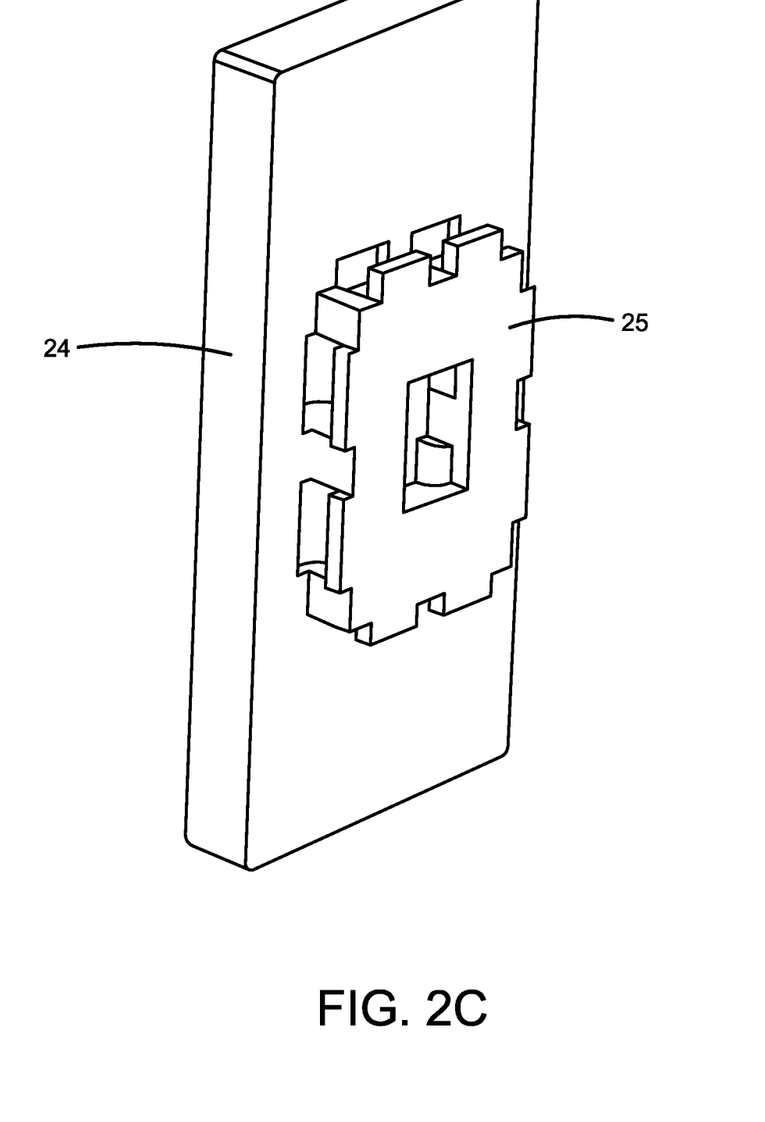
FIG. 2c depicts a perspective view of a mounting plate having a waffle-style mounting pattern according to the embodiments of the subject invention.

With reference to FIGS. 2a and 2b, the dispenser 10 may be attached to a supporting structure via mounting bracket 22 and a mounting plate 24. The mounting plate 24 may be a separate item that is readily separable from the mounting bracket 22 for easy removal of the dispenser 10 from the supporting structure. In one embodiment, a first side or first portion of the mounting plate 24 may be contoured to slide into slots 23 fashioned in the mounting bracket 22 for interlocking the dispenser 10 to the mounting plate 24. Alternate embodiments are contemplated where the mounting plate 24 includes a protruded waffle connector 25 (shown in FIG. 2c) designed to slide into slots 23 in a similar fashion.

The mounting plate 24 may include one or more holes 26 intended to receive fasteners, not shown, for securing the mounting plate 24 to a wall (not shown) or dispenser stand 19 as mentioned above. In operation, a second side or second portion of the mounting plate 24 may be affixed, i.e. fastened, to its intended support structure, where after the dispenser 10 is moved into position and secured to the mounting plate 24 by sliding or interlocking the two components together. Persons of skill in the art will recognize that other configurations of mounting bracket 22 and mounting plate 24 may be used without departing from the intended scope of coverage of the embodiments of the subject invention.

Figure 3:
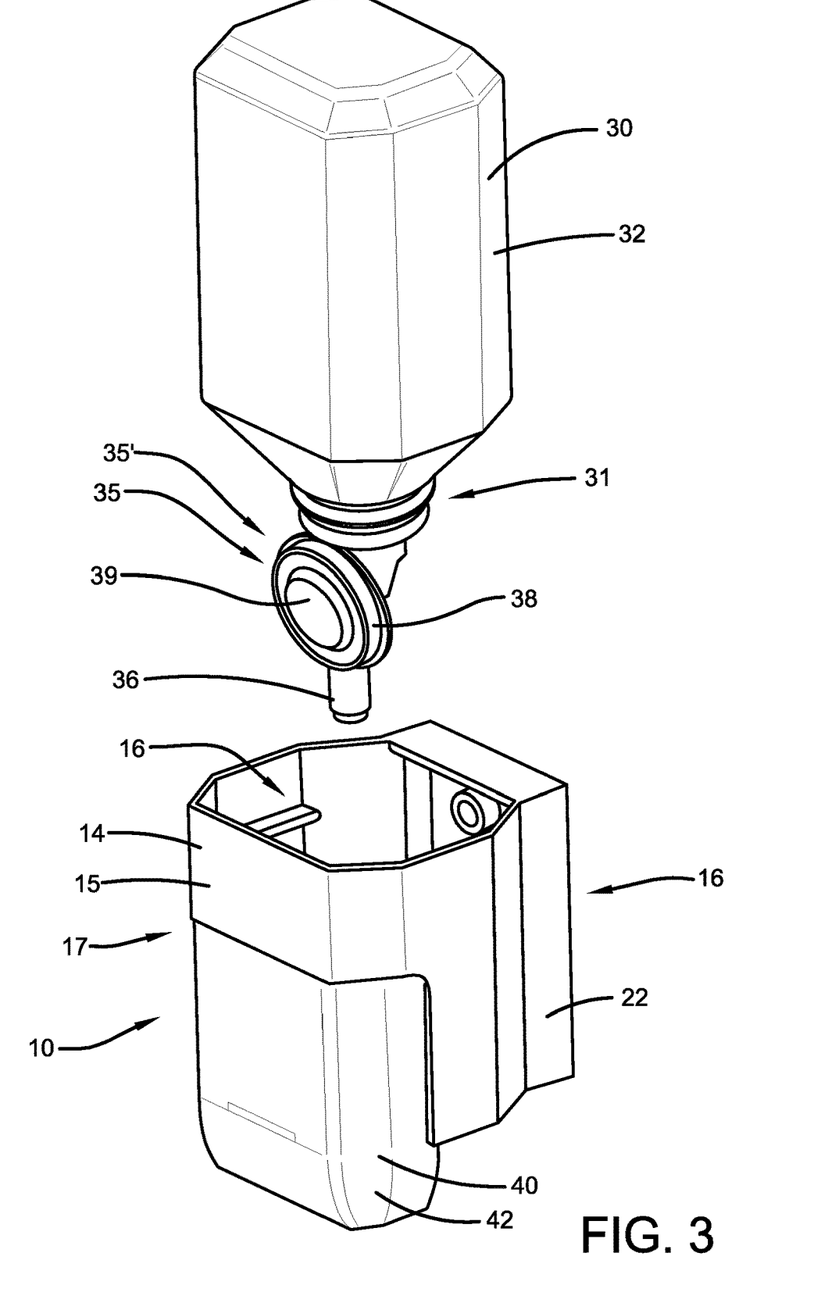
FIG. 3 depicts a front-side perspective view of a fluid dispenser and detached fluid reservoir showing the pump and nozzle according to the embodiments of the subject invention.

Referencing FIGS. 1 and 3, dispenser 10 utilizes a fluid reservoir 30 that contains a particular volume of hand care product. In one embodiment, the dispenser walls 15 are configured to form a concave region 16 into which the fluid reservoir 30 may be inserted. The concave region 16 as shown is generally enclosed and shrouds a portion of the fluid reservoir 30 as well as the internal components of the dispenser 10. However, more open configurations of the dispenser housing 14 may be incorporated that reveal the internal components of the dispenser and the fluid reservoir.

The dispenser housing 14 may also include a latch 20 for holding the fluid reservoir 30 in place during use. The latch 20 may be comprised one or more movable fingers, not shown, that engage a rim 31 (reference FIG. 3) of the fluid reservoir. Springs or other biasing device may be used to hold the fingers into retaining engagement with the reservoir 30. A portion of the latch 20 may extend to an outer surface of the dispenser 10 allowing service personal to depress the exposed portion of the latch 20 and thereby disengage the movable fingers from engagement with the rim 31. Thus, the reservoir may be removed and replaced with another reservoir.

With continued reference to FIG. 3, fluid reservoir 30 is comprised of a fluid tight container 32 having an opening fashioned at one end thereof. The container may be constructed from transparent material allowing service personnel to conveniently view how much product is remaining in the container 32. To dispense fluid, a pump 35 and nozzle 36 is attached to the open end of the container 32. When actuated, pump 35 ejects a measured amount of fluid through an internal channel formed in the nozzle 36.

In one embodiment, pump 35 is a dome pump referenced generally at 35'. The dome pump may include a rigid base 38 and flexible dome 39 that combine to define a pump chamber having a predetermined volume. An inlet and outlet, not shown, are formed in the rigid base which connect to the open end of the fluid reservoir 30 and the nozzle 36 respectively. Check valves, positioned in the fluid pathway near the inlet and outlet, ensure fluid flow from the reservoir 30 to the nozzle 36. In that the construction and operation of dome pumps are known in the art, no further explanation will be offered at this time. While one embodiment of a pumping mechanism has been described herein, persons of skill in the art will recognize that other types and configurations of the fluid pumping mechanisms may be suitably utilized with the dispenser 10.

Figure 4:
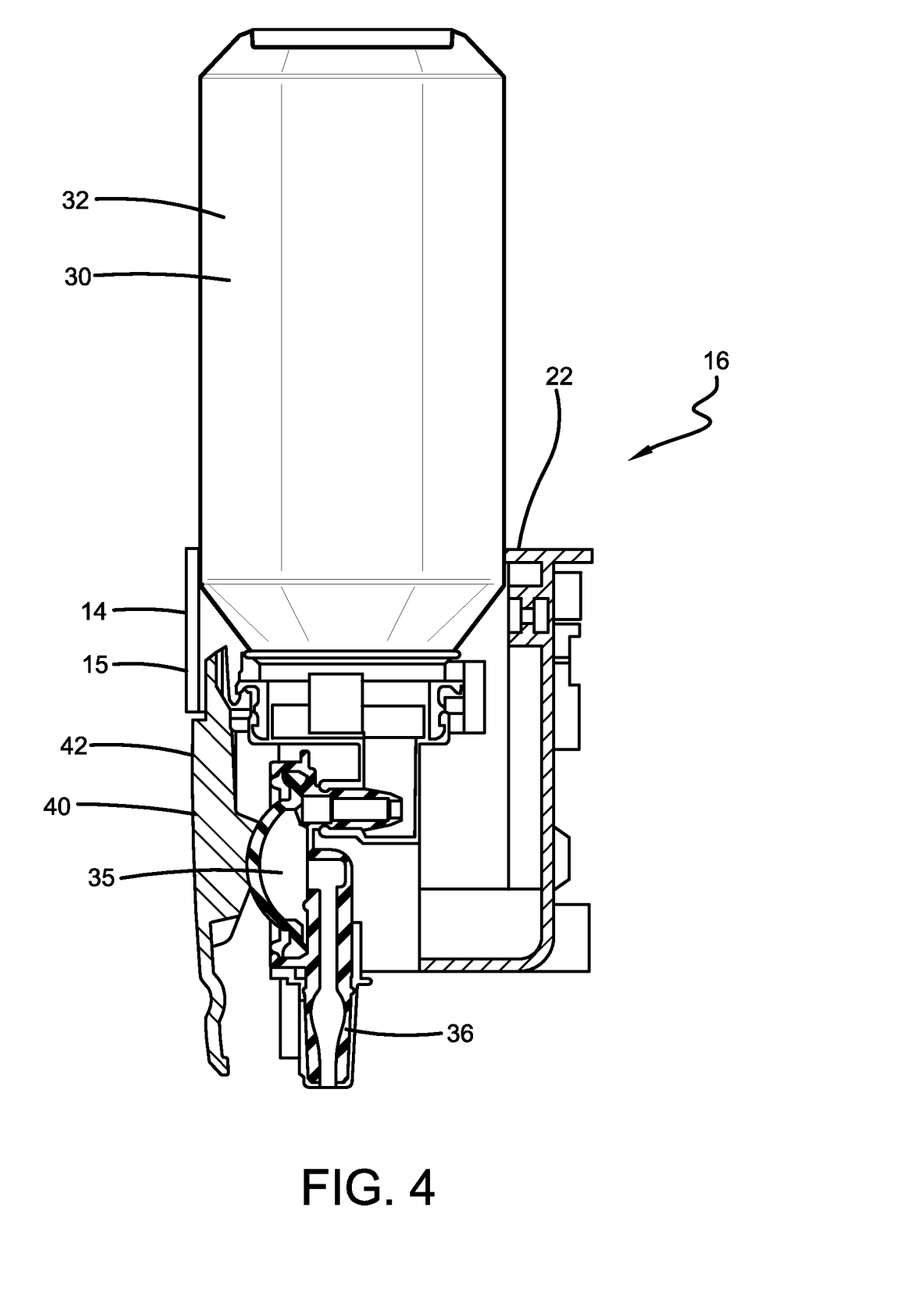
FIG. 4 is a schematic partial cutaway view of the fluid dispenser according to the embodiments of the subject invention.

Still referring to FIGS. 1 and 3 and now also to FIG. 4, a dispenser actuator 40 is shown, in an exemplary manner, attached to a front side 17 of the product dispenser 10. The dispenser actuator 40 may comprise a manually operated push bar 42 movably connected to the dispenser housing 14. In one embodiment, the push bar 42 may be pivotally connected to the dispenser housing 14. Alternatively, the push bar may slide or translate in a manner suitable for engaging the pump 35. In any configuration, the dispenser actuator 40 functions to actuate the pump 35 by depressing the flexible dome 39 of the pump chamber.

FIG. 4 shows one exemplary embodiment of the dispenser actuator 40. In this embodiment, the dispenser actuator 40 may include a contoured backside, which is configured to match the shape of the flexible dome 39. In this manner, as the dispenser actuator 40 is manually depressed, force from the users hand collapses the flexible dome 39 thereby pressurizing the fluid contained in the pump chamber. Fluid is then ejected through the nozzle when sufficient pressure is generated within the pump chamber.

Figure 5:
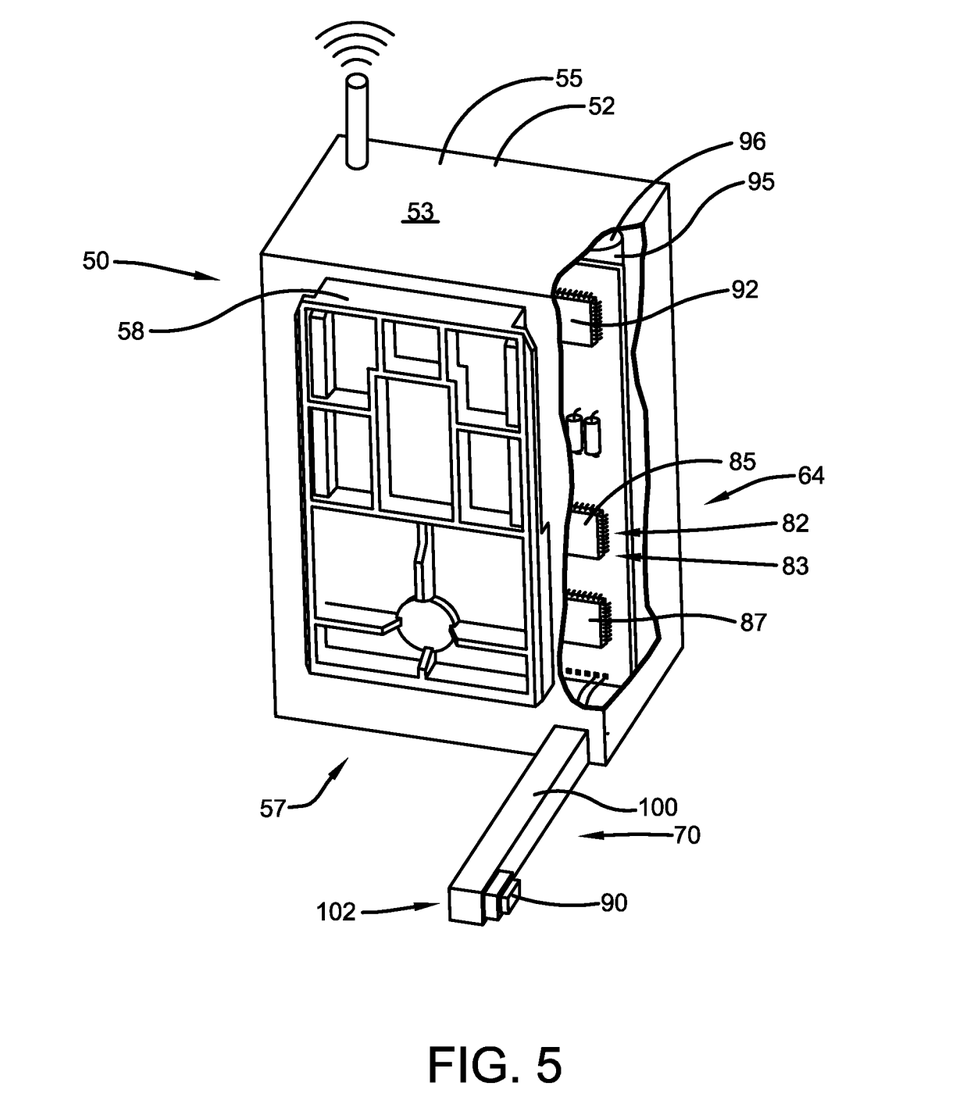
FIG. 5 is front side perspective view of a data collection module according to the embodiments of the subject invention.

With reference now to FIG. 5, a data collection module is shown generally at 50, which may be used for logging dispense events triggered by manual activation of the dispenser actuator 40. In one embodiment, the data collection module 50 may connect to the dispenser 10 at the rear side 16 of the dispenser housing 14 in a modular fashion. By modular it is meant that the data collection module 50 may be retrofitted into an existing dispenser 10 having been previously installed to a supporting structure as mentioned above. In one embodiment, the data collection module 50 may be connected between the mounting bracket 22 and the mounting plate 24. However, alternate embodiments are considered wherein the data collection module 50 is attached to another surface of the dispenser housing, like for example one of the side walls.

Figure 6:
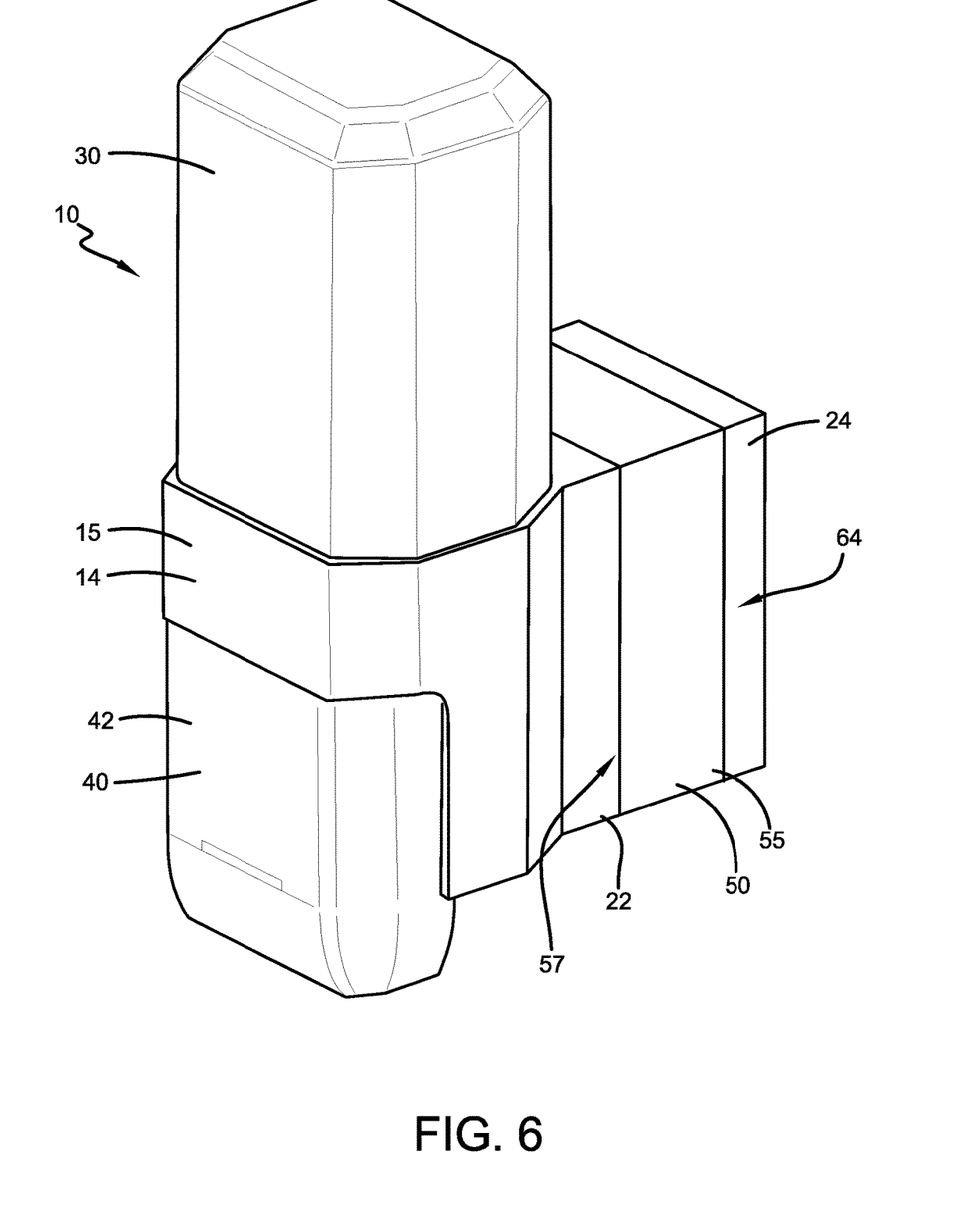
FIG. 6 is a perspective view of a data collection module connected between a fluid dispenser and mounting plate according to the embodiments of the subject invention.

Referencing FIGS. 5 and 6, the data collection module 50 includes a module housing 52. The module housing 52 may be comprised of a plurality of walls 53 forming an enclosure 55. A first mounting support 58 is fashioned on a first side 57 of the module housing 52, as shown in FIG. 5, for attaching the data collection module 50 to the dispenser 10. In one embodiment, the first mounting support 58 may extend outwardly from the module housing 52 for engaging the slots 23 in the mounting bracket 22. The first mounting support 58 may have a stepped configuration as depicted in FIG. 5. Alternatively, the first mounting support 58 may comprise a waffle connector 25 similar to the mounting plate 24 shown in FIG. 2c. Still, any configuration of first mounting support 28 may be incorporated into the data collection module 50 as is appropriate for connecting the module housing 52 to the mounting bracket 22 of the dispenser housing 14.

Figure 5A:
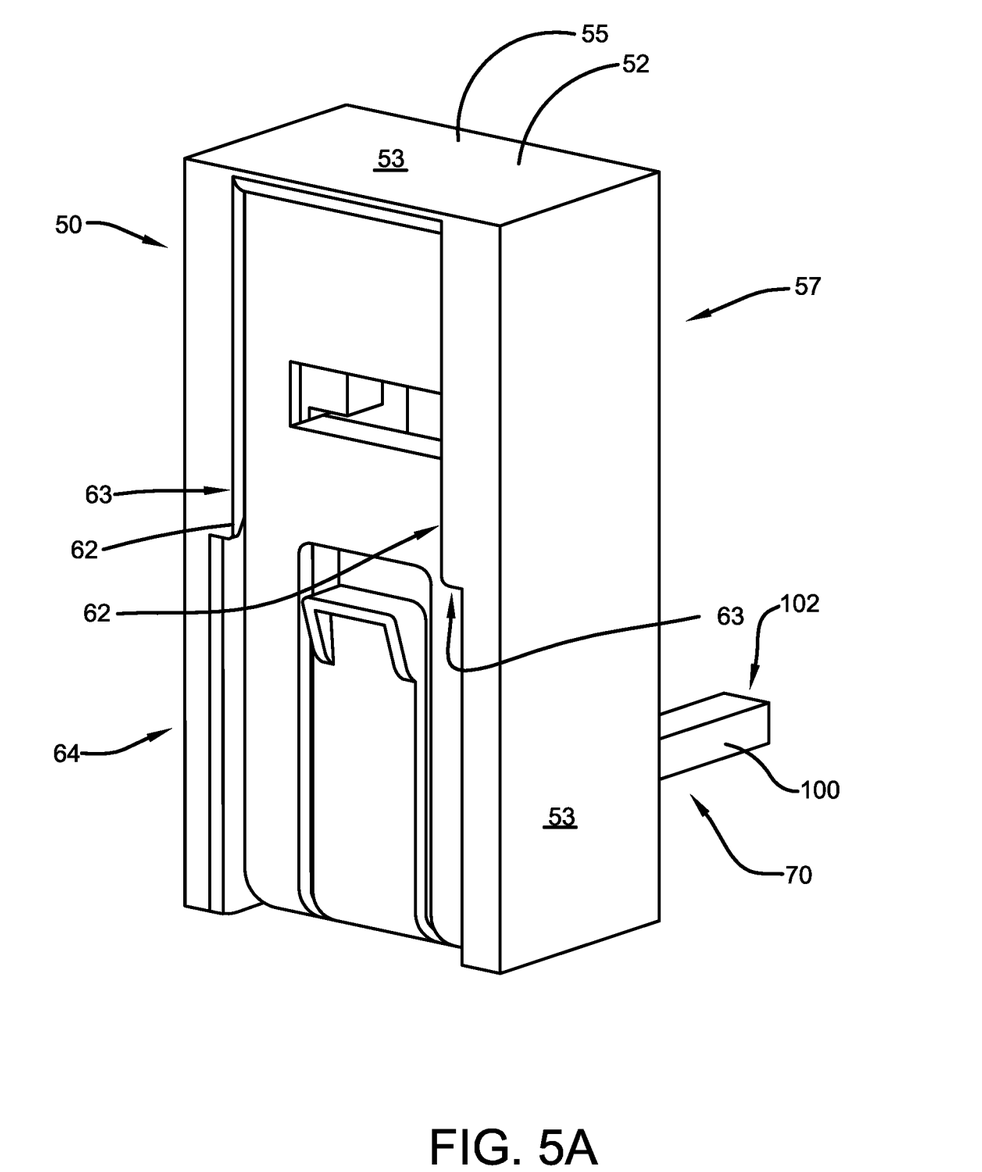
FIG. 5a is rear side perspective view of a data collection module according to the embodiments of the subject invention.

Now referencing FIGS. 5a and 6, a second mounting support 62 is fashioned on the distal second side 64 of the module housing 52 for use in connecting the module housing to a structure. Similar to the mounting bracket pattern shown in FIGS. 2a and 2b, the second mounting support 62 may include slots 63 having the same configuration as the slots 23 of the mounting bracket 22. In this way, the mounting plate 24 may be interconnected to the mounting bracket 22 or in a modular fashion may be interconnected to the second mounting support 62 instead of the mounting bracket 22. It should be construed that any configuration of second mounting support 62 may be chosen with sound engineering judgment as is appropriate for interconnecting the second mounting support 62 to the mounting bracket 22. Accordingly, persons of skill in the art will readily see the modularity of the dispenser 10 and the data collection module 50.

With continued reference to FIGS. 5 and 6, the data collection module 50 may include a detection instrument 70. The detection instrument 70 functions to detect dispense events. In one exemplary manner, a dispense event includes actuation of the dispenser actuator 40. As stated above, the data collection module 50 is modular, which is to say that the data collection module 50 may be retrofitted onto the dispenser at any time during or after installation of the dispenser 10. In this way, the detection instrument 70 functions to detect a dispense events when the data collection module 50 has been attached to the dispenser 10.

The detection instrument 70 may include one or more sensors 90 for detecting actuation of the dispenser actuator 40. As described above, the dispenser actuator 40 may include a push bar 42. The push bar 42 pivots or translates relative to the dispenser housing 14. When manually depressed, the push bar 42 engages the pump 35 to dispense fluid product. Accordingly, the sensors 90 detect movement or displacement of the dispenser actuator 40. It is noted that if the dispenser actuator 40 is not fully depressed, fluid product may not dispensed from the nozzle 36. As such, the detection instrument 70 and/or the sensor 90 may be configured to distinguish between a fully or partially depressed actuator 40 for use in determining whether or not a dispense event has occurred.

The sensor 90 may comprise any one of or a combination of sensor types. The types of sensors that may be incorporated into the data collection unit 50 may include both or either of contact and non-contact sensors. Examples of such sensors may include, but are not limited to: micro-switches, Hall-Effect sensors, Reed switches, Lasers, Infrared sensors, Sonic sensors and the like. Persons of skill in the art will recognize the application to other types of sensors without departing from the intended scope of coverage of the embodiments of the subject invention.

Depending on the type of sensor 90 used, the detection instrument 70 may include an arm 100 fixedly attached to and extending outwardly from the data collection module 50. The sensor 90 may be positioned on a distal end 102 of the arm 100. Accordingly, as the data collection module 50 is installed onto the dispenser 10, the arm 100 (and corresponding sensor) extends into the interior of the dispenser housing 14. It will be readily seen then that the arm 100 may be configured to position the sensor 90 proximal to the dispenser actuator 40 for use in detecting a dispense event as described above.

The sensor 90 may impinge on or directly contact a posterior surface of the dispenser actuator 40 for use in determining a dispense event. Alternatively, the dispenser actuator 40 may include a protrusion or other extended member that interacts directly with the arm 100 and/or sensor 90. One such example may comprise a cam or cammed surface. In another embodiment, a mechanical linkage or series of linkages may be interconnected between the dispenser actuator 40 and the arm 100 and/or sensor 90.

The arm 100 may be generally rigid and straight. In one specific embodiment, the arm 100 may not move with respect to the module housing 52. Other embodiments are contemplated where the arm 100 may be semi-rigid or even pliable for interacting with the dispenser actuator 40 or components thereof. The arm 100 may also be curved so as to position the sensor 90 in a manner appropriate for detecting movement or displacement of the dispenser actuator 40. It is noted that any configuration and/or type of material may be used to construct the arm 100 as chosen with sound engineering judgment.

In another embodiment of the subject invention, sensor 90 is positioned at or near the data collection module housing 52, which may be proximal to the mounting support. More specifically, sensor 90 may be received interior to the data collection module housing 52. To detect activation of the dispenser actuator 40, arm 100 is designed to move in conjunction with the dispenser actuator 40. In this way, activating the dispenser actuator 40 translates into movement of the arm 100, which is detected by the sensor 90. In other words, the arm 100 is movably connected between the dispenser actuator 40 and the sensor 90. Thereafter, data from the output of the sensor 90 is communicated to electronic circuitry incorporated into the data collection module 50 as will be discussed further below.

Figure 5B:
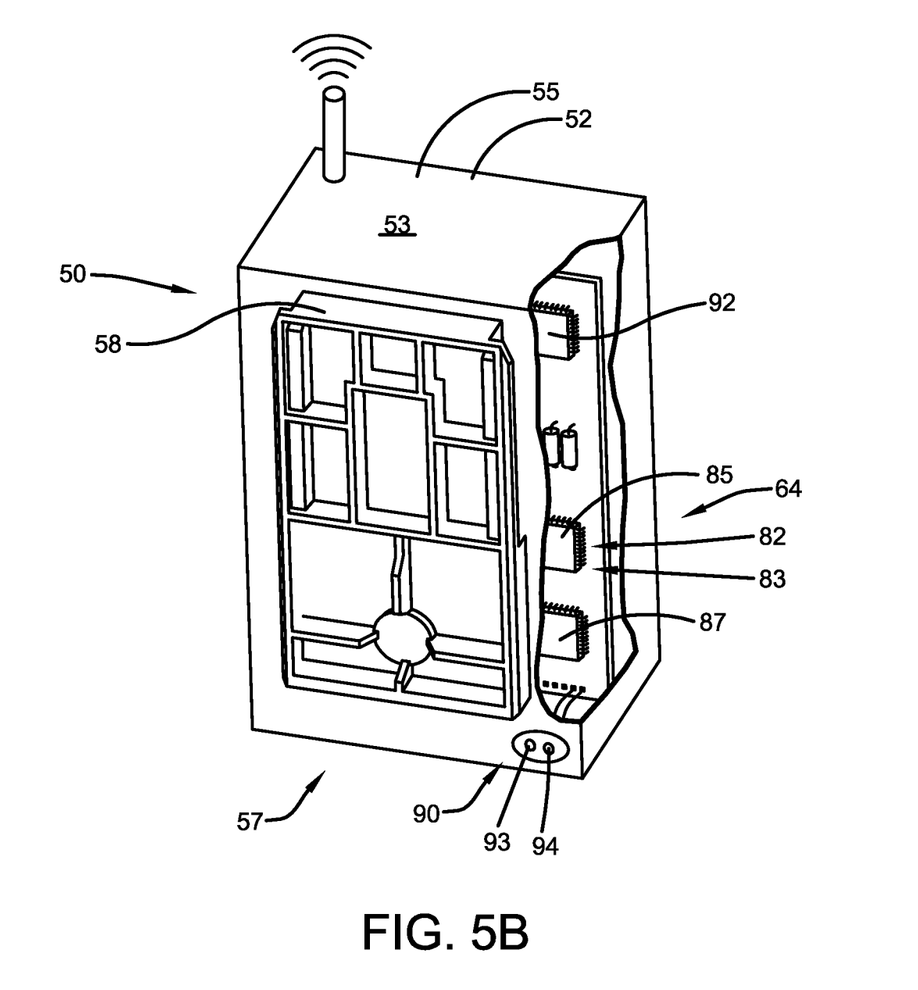
FIG. 5b is front side perspective view of a data collection module according to the embodiments of the subject invention.

With reference now to FIG. 5b, in another embodiment of the subject invention, the sensor 90 is similarly positioned near the data collection module housing 52, which may be interior to the data collection module housing 52. However, the sensor 90 in this embodiment is operable to detect activation of the dispenser actuator 40 without the use of arm 100. The sensor 90, in an exemplary manner, may comprise a laser sensor or Hall-Effect sensor that emits a field of detection, which is used to detect activation of the dispenser actuator 40. Of course, other types of non-contact sensors may be used. More specifically, the field of detection emitted by the sensor 90 may detect displacement or any form of movement of the dispenser actuator 40. In operation, the sensor 90 may include an emitter 93 and a detector 94. The detector 94 may be set up to read a change in the intensity of the emitted field, which varies when an object changes its position. Still, other methods of detecting displacement or movement will be apparent to persons of skill in the art.

Figure 7:
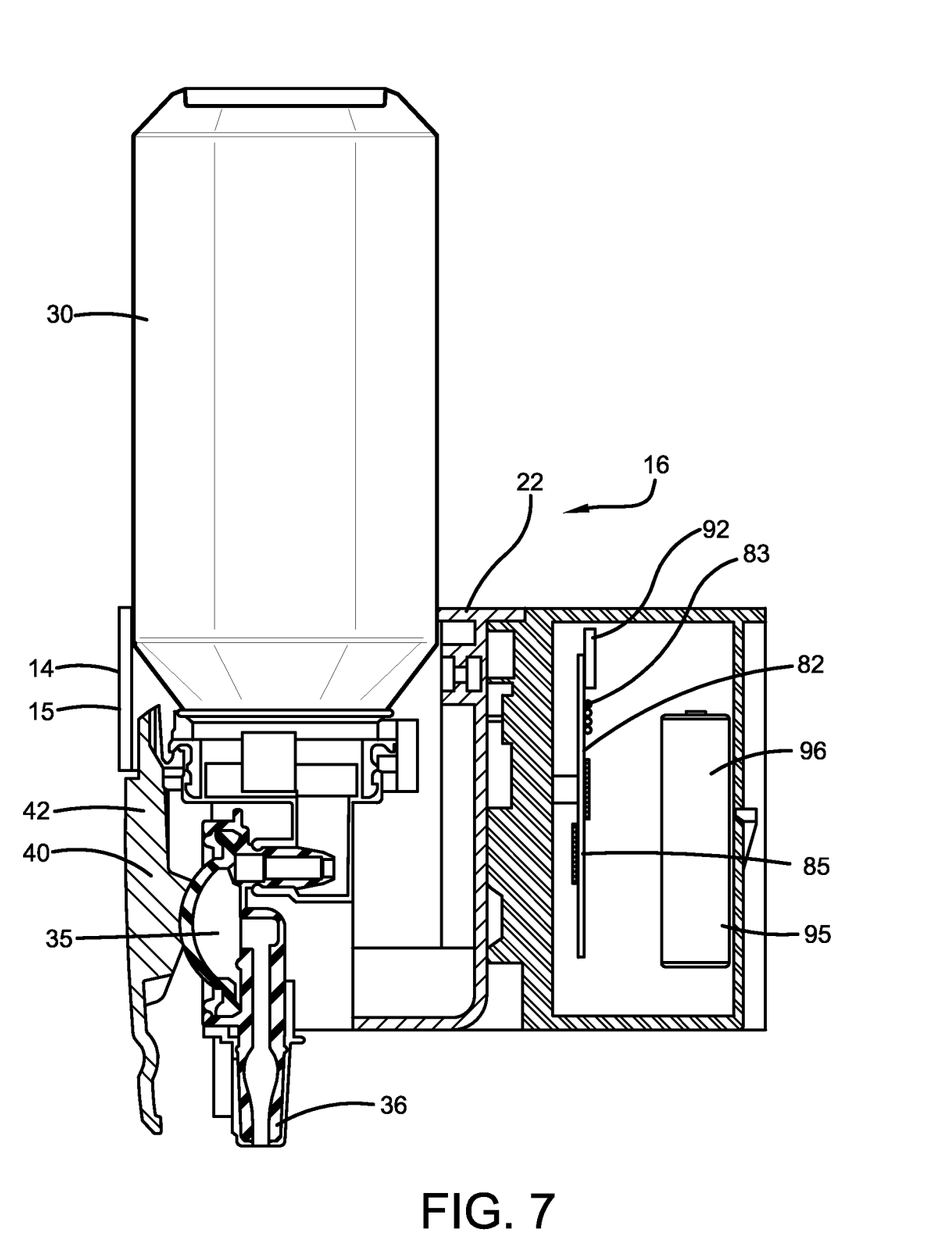
FIG. 7 is a schematic partial cutaway view of a fluid dispenser and data collection module attached to a posterior side of the fluid dispenser according to the embodiments of the subject invention.

With reference again to FIG. 5 and now also to FIG. 7, the data collection module 50 includes electronic circuitry, indicated generally at 82. The electronic circuitry 82 may comprise digital electronic circuitry 83 designed to receive and process data relating to dispense events. In one embodiment, the digital electronic circuitry 83 functions to receive output signals from the sensor 90. Persons of skill in the art will understand that different sensors output different forms of electrical signals. As such, electronic circuitry 82 may include various types of electronic circuitry designed to receive and/or condition sensor signals. One example of such circuitry may comprise analog to digital converters. However, persons of skill in the art will understand the use and implementation of a wide array of circuitry as may be necessary for capturing data pertaining to a dispense event.

The electronic circuitry 82, 83 may further comprise electronic data storage 85 or memory 85. In one embodiment, memory 85 may include volatile memory, like for example SDRAM, along with the requisite supporting circuitry. Alternatively, the storage of data may be implemented using flash memory or other non-volatile forms of data storage. Still, any type of electronic data storage 85 may be incorporated into the electronic circuitry 82, 83 as is appropriate for use with the various embodiments of the subject invention.

Electronic circuitry 83 used in the data collection module 50 may further comprise a logic processor 87, which in one embodiment may be a digital microprocessor. Accordingly, the logic processor 87 may be programmable. In a manner known in the art, the logic processor 87 is in communication with memory 85. Signals from the output of the sensor 90 may be stored in memory 85 for transmission to a remote network or other external data system, not shown.

The types of the data stored in memory may include data related to activation of the dispenser 10, as well as other types of data. For example, the data collection module 50 may capture data about the user of the dispenser 10. In a hospital environment, the user may be a healthcare worker (HCW) or a patient. As such, circuitry may be included in the data collection module 50 that receives data wirelessly from a hospital identification badge or patient bracelet.

In one embodiment, circuitry incorporated into the data collection module 50 keeps track of the time of day and/or date. When a dispense event occurs, the logic processor 87 may be programmed to integrate the time and/or date data with the dispense event data. This is referred to as a time stamp. In this way, the data collection module 50 is operable to provide time-weighted data, which may be analyzed to measure compliance in the use of hand hygiene products.

The data collection module circuitry 83 may further include a transmitter 92 for communicating data to the remote network. In one embodiment, the transmitter 92 may be a wireless transmitter. Data received by the data collection module 50 may be sent to a remote network automatically as the data is received. In an alternate embodiment, the transmitter 92 may include one or more data ports, not shown, adapted to receive a data cable, also not shown. Once communication has been established with the data port, data may be communicated from the memory 85 to a remote network via the logic processor 87.

Power supplied to the data collection module 50 may come from an onboard power source 95. In one embodiment, the onboard power source may include photoelectric cells. Most notably, however, the power source 95 comprises one or more batteries 96, also referred to as an electrical power storage device. The batteries 96 may reside on a circuit board received by the data collection module housing 52 or may be mounted directly to the housing 52. In any instance, the batteries 96 may provide power to operate the sensors 90 and the electronic circuitry 82, 83. Persons of skill in the art will recognize the use of other embodiments of electrical power storage devices without departing from the intended scope of coverage of the embodiments of the subject invention.

It will be apparent to those skilled in the art that various modifications and variations can be made to the embodiments described herein without departing from the spirit and the scope of the claimed subject matter. Thus, it is intended that the specification cover the modifications and variations of the various embodiments described herein provided such modifications and variations come within the scope of the appended claims and their equivalents.

What is claimed is:

1. A fluid dispensing system, comprising:
a dispenser housing having one or more walls supporting an associated fluid reservoir and a pump, the dispenser housing having a mounting bracket extending therefrom;
a dispenser actuator connected to the dispenser housing for engaging the pump;
a mounting plate having a first side and a second side, wherein:
the first side of the mounting plate includes a first mounting surface for attaching the mounting plate to an associated structure, and
the second side of the mounting plate includes a second mounting surface adapted to receive the mounting bracket for supporting the dispenser housing; and
a data collection module selectively mountable between the dispenser housing and the mounting plate, the data collection module including:
a module housing defining an enclosure for receiving digital electronic circuitry;
a detection instrument detecting activation of the dispenser actuator when the data collection module is attached to the dispenser housing, the detection instrument having an output indicating activation of the dispenser actuator, wherein the detection instrument comprises:
a generally rigid arm extending between the module housing and the dispenser actuator when the module housing is attached to the dispenser housing; and
a sensor operatively connected to the generally rigid arm for detecting activation of the dispenser actuator; and
the digital electronic circuitry including memory for storing data representing the output indicating activation of the dispenser actuator and a processor for use in communicating the data to an associated external device.

2. The fluid dispensing system as defined in claim 1, wherein the digital electronic circuitry further comprises:
a transmitter for wirelessly communicating the data to an associated network.

3. The fluid dispensing system as defined in claim 1, wherein the digital electronic circuitry further comprises:
a circuit for generating an electronic time stamp.

4. The fluid dispensing system as defined in claim 1, wherein:
the enclosure of the module housing includes a first mounting support adapted to attach to the mounting bracket of the dispenser housing in place of attaching the mounting plate, and
the enclosure includes a second mounting support adapted to attach to the mounting plate in place of attaching the dispenser housing.

5. The fluid dispensing system as defined in claim 4, wherein the first mounting support and the second mounting support are fashioned on distal sides of the enclosure.

6. The fluid dispensing system as defined in claim 1, wherein the dispenser actuator comprises a push bar pivotally mounted to the dispenser housing, and
wherein the sensor includes a switch mounted on an end of the generally rigid arm, wherein the sensor is mounted proximal to the push bar for detecting movement of the push bar.

7. The fluid dispensing system as defined in claim 1, wherein the sensor is a non-contact sensor for detecting displacement of the dispenser actuator.

8. The fluid dispensing system as defined in claim 1, wherein the sensor is operatively connected to the digital electronic circuitry; and
the generally rigid arm is movably connected between the dispenser actuator and the sensor for translating a displacement of the dispenser actuator to the sensor.

9. The fluid dispensing system as defined in claim 1, wherein the data collection module further comprises:
an onboard electrical power storage device electrically connected to supply power to the digital electronic circuitry.

10. A data collection module for capturing dispense event information from an associated fluid dispenser having a dispenser housing and a dispenser actuator, the data collection module comprising:
a module housing having one or more walls defining an enclosure, wherein the module housing includes a first mounting support for connecting the module housing to the associated fluid dispenser and a second mounting support for connecting the module housing to an associated structure;
a detection instrument for detecting activation of the dispenser actuator when the data collection module is attached to the dispenser housing, the detection instrument having an output indicating activation of the dispenser actuator, wherein the detection instrument comprises:
a generally rigid arm extending from the data collection module, wherein the generally rigid arm extends into the dispenser housing when the module housing is attached to the associated fluid dispenser; and
a sensor operatively connected to the generally rigid arm and positioned to detect activation of the dispenser actuator;
digital electronic circuitry including memory for storing data representing the output indicating activation of the dispenser actuator and a processor for use in communicating the data to an associated external network, wherein:
the digital electronic circuitry is received at least partially within the enclosure, and
the sensor is in communication with the digital electronic circuitry; and
an electrical power storage device operatively connected to supply electrical power to the digital electronic circuitry.

11. The data collection module as defined in claim 10, wherein:
the generally rigid arm defines a first end and a second distal end,
the generally rigid arm is fixedly attached to the module housing at the first end, and
the sensor is affixed to the second distal end of the generally rigid arm for detecting activation of the dispenser actuator.

12. The data collection module as defined in claim 10, wherein the sensor comprises a switch having an electrical output operatively communicated to the digital electronic circuitry.

13. The data collection module as defined in claim 10, wherein the sensor is a non-contact sensor mounted to the enclosure and mounted proximal to the first mounting support, wherein the non-contact sensor emits a field of detection operable to detect activation of the dispenser actuator.

14. The data collection module as defined in claim 13, wherein the non-contact sensor detects displacement of the dispenser actuator.

15. The data collection module as defined in claim 10, wherein the digital electronic circuitry further comprises:
a transmitter for wirelessly communicating the data to an associated network.

16. The data collection module as defined in claim 10, wherein the digital electronic circuitry further comprises:
a circuit for generating an electronic time stamp.

17. A data collection module for capturing dispense event information from an associated fluid dispenser having a dispenser housing and a dispenser actuator, the data collection module comprising:
a module housing having one or more walls defining an enclosure, wherein the module housing includes a first mounting support for connecting the module housing to the associated fluid dispenser and a second mounting support for connecting the module housing to an associated structure;
a detection instrument for detecting activation of the dispenser actuator when the data collection module is attached to the dispenser housing, the detection instrument having an output indicating activation of the dispenser actuator, wherein the detection instrument comprises:
a generally rigid arm moveably connected to translate displacement of the dispenser actuator; and
a sensor operatively connected to sense movement of the generally rigid arm;
digital electronic circuitry including memory for storing data representing the output indicating activation of the dispenser actuator and a processor for use in communicating the data to an associated external network, wherein:
the digital electronic circuitry is received at least partially within the enclosure, and the sensor is in operable communication with the digital electronic circuitry; and an electrical power storage device operatively connected to supply electrical power to the digital electronic circuitry.

18. The data collection module as defined in claim 17, wherein the digital electronic circuitry further comprises:

a transmitter for wirelessly communicating the data to an associated network.

19. The data collection module as defined in claim 17, wherein the digital electronic circuitry further comprises:

a circuit for generating an electronic time stamp.

20. The data collection module as defined in claim 17, wherein the sensor is a non-contact sensor.

\* \* \* \* \*